(12) United States Patent
Vissa et al.

(10) Patent No.: US 10,646,161 B1
(45) Date of Patent: May 12, 2020

(54) WEARABLE ARTICLE FOR DETERMINING A TASK

(71) Applicant: Motorola Mobility LLC, Chicago, IL (US)

(72) Inventors: Sudhir C. Vissa, Bensenville, IL (US); Vivek Kumar Tyagi, Chicago, IL (US); Scott Patrick DeBates, Crystal Lake, IL (US); Douglas Alfred Lautner, Round Lake, IL (US)

(73) Assignee: Motorola Mobility LLC

( * ) Notice: Subject to any disclaimer, the term of this patent is extended or adjusted under 35 U.S.C. 154(b) by 44 days.

(21) Appl. No.: 16/168,569

(22) Filed: Oct. 23, 2018

(51) Int. Cl.
*A61B 5/00* (2006.01)
*G06F 3/01* (2006.01)
*G16H 40/60* (2018.01)
*A61B 5/11* (2006.01)
*A61M 5/178* (2006.01)

(52) U.S. Cl.
CPC .............. *A61B 5/6806* (2013.01); *A61B 5/11* (2013.01); *A61M 5/178* (2013.01); *G06F 3/014* (2013.01); *G16H 40/60* (2018.01)

(58) Field of Classification Search
CPC ....... A61B 5/68; A61B 5/6801; A61B 5/6802; A61B 5/6806; A61M 5/178
See application file for complete search history.

(56) References Cited

U.S. PATENT DOCUMENTS

| | | | |
|---|---|---|---|
| 2013/0197399 A1* | 8/2013 | Montgomery | A61B 5/1121 600/595 |
| 2016/0354562 A1* | 12/2016 | Morrison | A61M 15/0001 |
| 2018/0092802 A1* | 4/2018 | Giacometti | A61H 31/007 |
| 2018/0280607 A1* | 10/2018 | Richards | A61M 5/24 |

OTHER PUBLICATIONS

"Savvy Mobile Medication Workstation", Retrieved at: https://www.omnicell.com/Products/Medication_Dispensing/Automated_Medication_Dispensing/Savvy_Mobile_Medication_System.aspx—on Jul. 27, 2017, 3 pages.
"Pumping Up: How Hospitals are Using "Smart" Infusion Pumps to Help Improve Medication Delivery Safety and Hospital Efficiency", Retrieved at: https://www.baxter.com/news-media/newsroom/featured-stories/features_sigma_spectrum.page, Sep. 2014, 5 pages.

* cited by examiner

*Primary Examiner* — Andrew W Bee
(74) *Attorney, Agent, or Firm* — SBMC

(57) ABSTRACT

In aspects of a wearable article for determining a task, a system includes a delivery device usable to administer a liquid responsive to an applied force, and includes a wearable article with multiple sensors to detect movements of the wearable article and handling of the delivery device. A task determination module is implemented to receive sensor data identifying the movements of the wearable article and the applied force, and can determine a task from a set of tasks associated with the delivery device that corresponds to the movements of the wearable article. The task determination module can then determine whether the task was performed correctly based on a comparison of the sensor data to a correct pattern of use for the task.

20 Claims, 4 Drawing Sheets

WEARABLE ARTICLE FOR DETERMINING A TASK

BACKGROUND

In a healthcare setting, professionals rely on practiced techniques to provide proper delivery of care. However, training these techniques and ensuring they are correctly performed over the long term is difficult to monitor, and improper training can have severe consequences. For instance, an amount of pressure needed to deliver medicine using a syringe to an infant is minimal and incorrect delivery can cause devastating effects. Training a new healthcare professional to perform such delicate tasks is made difficult by the lack of quantifiable instructions for both how the task should be performed and how the trainee is performing the task. Training healthcare professionals to develop proper techniques, particularly for distributing medicine, and ensuring that practiced professionals are properly delivering care, are ongoing concerns in the healthcare profession.

BRIEF DESCRIPTION OF THE DRAWINGS

Implementations of a wearable article for determining a task are described with reference to the following Figures. The same numbers may be used throughout to reference like features and components shown in the Figures.

DETAILED DESCRIPTION

Figure 1:
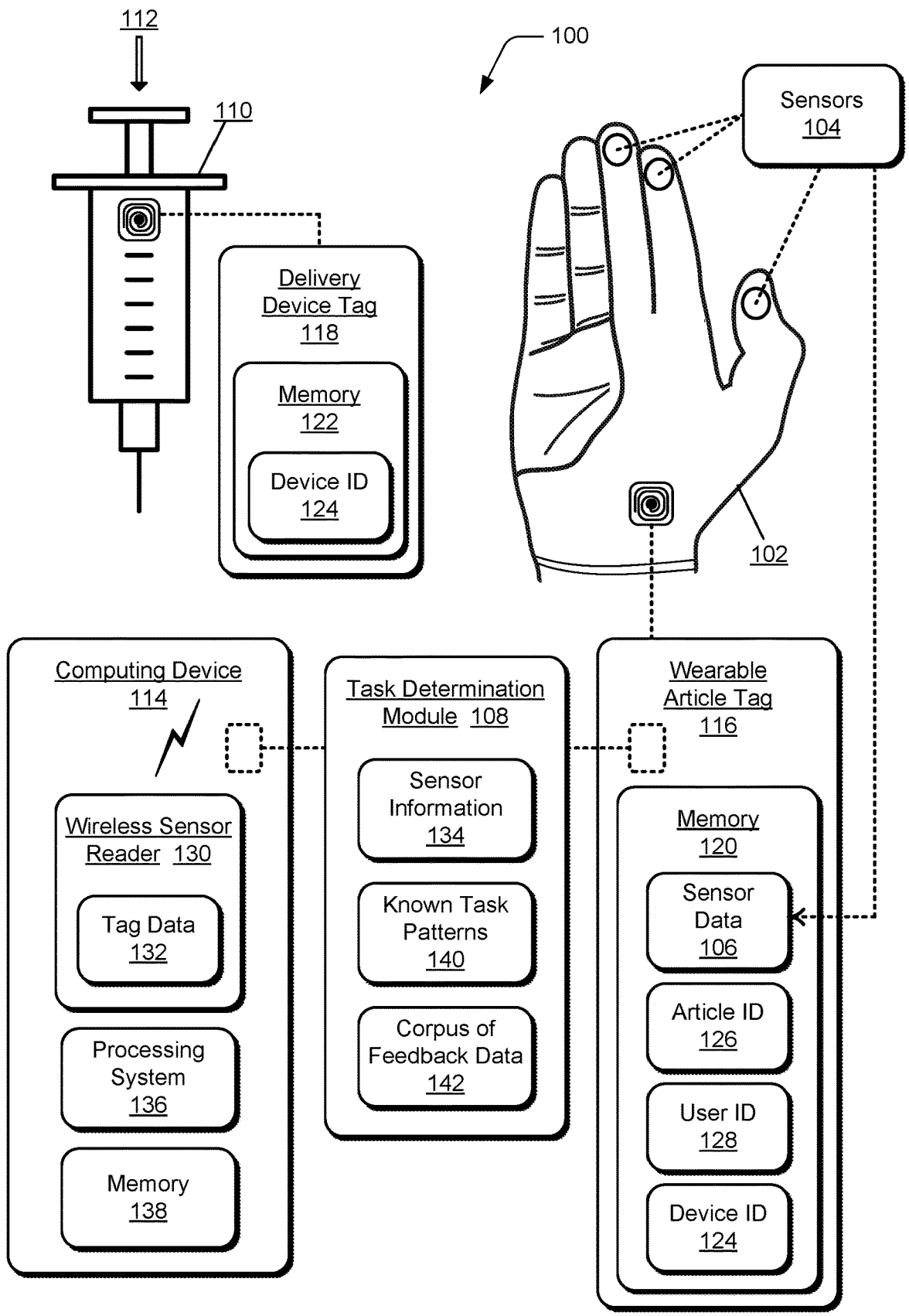
FIG. 1 illustrates an example environment that can be used to implement a wearable article for determining a task as described herein.

Implementations of a wearable article for determining a task are described, and techniques that allow for collection and analysis of data related to the performance of the task. For instance, a user may wear a wearable article, such as a glove or partial glove with integrated sensors that collect data from which a task performed by the user can be determined, and whether the task was performed correctly. In a medical environment, wearing gloves is already an established practice, and implementing the wearable article as a glove, as described herein, enables advanced data collection for the purpose of both training and ensuring that tasks are correctly performed.

Generally, a system of sensors embedded or integrated in a wearable article can detect movements of the wearable article as well as pressure applied by a user wearing the wearable article. Sensor data from the sensors can be communicated to a task determination module which can be implemented on the wearable article, or at a computing device with additional processing power, such as a mobile phone or computing device. The task determination module can use the sensor data to determine a type of task performed by the user while wearing the wearable article. The wearable article can be associated with a particular user once it has been put on, such as by communication with an employee badge or mobile phone of the user from which a user identifier can be determined. Associating the wearable article with the user enables wear session tracking so the actions associated with the user while wearing the wearable article can be analyzed.

The task determination module may also receive an indication of one or more tools used by the user, such as a delivery device (e.g., a syringe) that can be used to administer a liquid, solution, or other type of malleable material responsive to applied pressure. The wearable article and the delivery device may each be associated with wireless radio based tags that uniquely identify the associated item. Additional wireless radio based tags may identify a number of different tools, such as medication containers, room identifiers, machines, and so on. These additional wireless radio based tags can be used to track equipment and medicines, as well as identify a location of the wearable article, such as being in a particular patient's room.

The task determination module can determine, based on the received sensor data, and, optionally, indications from the wireless radio based tags, a task being performed by the user of the wearable article. For instance, the sensor data may indicate that the user is putting on the wearable article, that the user has picked up the delivery device while wearing the wearable article, and that the user has administered the liquid into a particular substance using the delivery device. The sensor data may then be compared to a corpus of feedback data that was previously collected or entered regarding the identified task to determine whether the task has been performed correctly based on the sensor data falling within an acceptable range, as determined from the previous corpus of feedback data. Feedback in the form of audio and/or visual notifications may then be provided to a user based on the determination, such as an indication of how the task may be performed better, or may be provided to alert the user that the task has been performed correctly or incorrectly.

In implementations, the sensor data detected while a user is wearing a wearable article can be analyzed to determine a task performed by the user wearing the wearable article. For instance, the sensors may include one or more force sensors and/or one or more microelectromechanical system (MEMS) sensors which can detect how much pressure a user applies to an object, as well as when a user bends their fingers while wearing the wearable article. This sensor data can be compared to known task patterns or use in order to identify a particular task being performed. The task may be one of a set of tasks associated with the wearable article and the delivery device. For instance, if the delivery device is a syringe, the set of tasks may include picking the syringe up from a storage location, loading the syringe with a liquid (e.g., medicine or other solution), ejecting the liquid from the syringe into the air, and injecting the liquid from the syringe into a patient. Although generally described in the context of medical devices and medicine delivery applications, the techniques described herein are applicable in a multitude of environments, such as in construction, manufacturing, product assembly, and in any environment in which a user handles a tool or device to accomplish a task.

In further implementations, the sensor data recorded during the performance of a task may be compared to a corpus of feedback data related to the task. For instance, the corpus of feedback data may be a collection of data taken during the performance of the same task performed by one or more individuals, such as during previous times when the same user has performed the same task, when different users have performed the task, and/or the data may be a range of values explicitly entered as correct values. The corpus of feedback data indicates an acceptable range of sensor data values for each task that can be determined from the corpus of data or can be manually entered. After comparing the sensor data to the corpus of feedback data and/or to the acceptable range of values, the user can be notified of how well the task was performed. For instance the notification may be an audible and/or visual indication that the task was performed within an acceptable range of performance, or that the task was performed outside of the acceptable range. The notification may take any desired form, such as in the form of haptic feedback via the wearable article, or an audible or visual alert sent to a computing device, such as a mobile phone or a computing device.

The sensor data can further be stored by the task determination module as part of the corpus of feedback data, and additional data can be associated with the sensor data. For instance, patient outcomes can be included as part of the data in order to better determine the acceptable range of performance for a particular task. By including such data in addition to the data collected via the sensors integrated with the wearable article, the wearable article and the task determination module can be leveraged to alert a healthcare professional if a task has been performed incorrectly, and also can be used to determine optimal techniques, such as optimal parameters for injecting certain medications. Further, the feedback can help in the training process by quantifying a difference between how a task was performed by a trainee and the correct way the task is performed, or may be used to compare previous performances of the task by the trainee to the current performance to identify changes in the technique.

While features and concepts of a wearable article for determining a task can be implemented in any number of different devices, systems, environments, and/or configurations, implementations of a wearable article for determining a task are described in the context of the following example devices, systems, and methods.

FIG. 1 illustrates an example environment 100 in which aspects of a wearable article for determining a task can be implemented. The example environment 100 may be implemented in any environment where a person may wish to learn or confirm correct performance of a task. As noted above, although generally described in the context of medical devices and medicine delivery applications, the techniques described herein are applicable in a multitude of environments, such as in construction, manufacturing, product assembly, and in any environment in which a user handles a tool or device to accomplish a task. In this example, the environment 100 includes wearable article 102 integrated with multiple sensors 104. The wearable article 102, may for instance, be implemented as a glove, or a partial glove as shown, to be worn in a hospital or other healthcare setting.

The example wearable article 102 covers at least a thumb, index, and middle fingers with the sensors 104 included in the digits of the wearable article 102. This allows the wearable article 102 to detect movements and other actions performed by a user wearing the wearable article 102. Of course, the wearable article 102 may cover more or fewer digits of the user and may include sensors integrated throughout the wearable article, such as along the palm or back of the hand and in the band around the wrist. Alternately, the wearable article 102 may take the form of a sock, body suit, watch, and so on, and the sensors may be integrated in the wearable article in any suitable configuration.

In this example, the wearable article 102 includes the sensors 104 that generate sensor data 106 from which a task determination module 108 can determine a task being performed from combination of movements of the wearable article 102 and handling of a delivery device 110. In this example environment, the delivery device 110 is illustrated as a syringe that can be used to administer medicine in liquid form responsive to an applied force 112 on a plunger of the syringe. The sensors 104 may be implemented as, but are not limited to, microelectromechanical system (MEMS) sensors including a gyroscope, an accelerometer, motion sensors, force sensors, and electromyography (EMG) sensors. Additional sensors may include infrared (IR) sensors, proximity sensors, a magnetometer, cameras, and temperature sensors.

The sensor data 106 may indicate movement performed by the user wearing the wearable article 102, the force 112 applied through the wearable article 102 by the user, and muscle activation of the user. The sensor data 106 may be accessible to the user via a computing device 114 in real-time, or an analysis may be provided after completion of a task. The sensors 104 may also provide the sensor data 106 in both vector and/or quantitative forms. For instance, the MEMS sensors can provide information about an orientation of the wearable article 102 in space and a direction, while the force sensors can provide information about an amount of force or pressure applied as well as a direction in which the force is applied.

The sensors 104 can be integrated in a variety of locations on the wearable article 102. MEMS and pressure sensors may be placed on the fingertips of the wearable article 102, and/or may be spread out to cover the center of each finger. Additionally, the EMG sensors can be included around a wrist of the wearable article 102 to provide information about muscle activation to better detect the positioning of a user's hand. The sensors 104 enable the task determination module 108 to determine a rate at which a liquid is administered using the delivery device 110 (e.g., a number of seconds it takes to administer a set amount of the liquid to a patient). The delivery device 110 is an example of a tool that can be used during the performance of a task while wearing the wearable article 102. For instance, the delivery device 110 may be a syringe that is used to administer injections. The delivery device 110 may be any of a variety of tools for use in the medical setting and beyond, such as tools used in a variety of medical practices, applying icing in baking, applying glue in crafting, and so on.

Each of the wearable article 102 and the delivery device 110 are equipped with a wireless radio based tag, wearable article tag 116 and delivery device tag 118 respectively. Generally, wireless radio based tags are small electronic tags that record the sensor data 106 and other sensor information in a memory on each respective tag. For example, the wearable article tag 116 includes a memory 120 that stores the sensor data 106 received from the sensors 104 of the wearable article. The delivery device tag 118 includes a memory 122, which can be used to store a device identifier 124 of the delivery device 110, as well as a state of the delivery device. For instance, the current state may indicate that the delivery device 110 is unused, has been filled, or has been used. Similarly, the memory 120 of the wearable article tag 116 can be used to store an article identifier 126 of the wearable article 102, as well as a copy of the device identifier 124 and/or a user identifier 128 of a corresponding user who wears the wearable article 102 and handles the delivery device 110.

The wireless radio based tags (e.g., the wearable article tag 116 and the delivery device tag 118) can be implemented for various different radio-based, wireless tag signaling, such as with radio frequency identification (RFID), LTE, Near Field Communication (NFC), Real-time Locating System (RTLS), Bluetooth™ devices, or any other type of wireless sensor. The computing device 114 and/or the task determination module 108 can be equipped with a wireless sensor reader 130 (such as an RFID reader). In addition to an RFID implementation, the wireless sensor reader 130 may be implemented for any type of wireless communication technology, such as Wi-Fi, Bluetooth™, Mobile Broadband, LTE, Near Field Communication (NFC), Real-time Locating System (RTLS), or any other wireless radio system or format for communication via respective wireless networks. Generally, the task determination module 108 and/or the computing device 114 (e.g., a mobile phone) implements the wireless sensor reader 130 that includes a radio device, antenna, and chipset implemented for cellular, wireless, and/or other network communication with other devices, networks, and services.

The wireless sensor reader 130 is implemented to transmit interrogation signals as broadcast messages requesting the wireless radio based tags, such as the wearable article tag 116 and the delivery device tag 118, return the tag data 132 stored in the respective tag memories 120, 122. A wireless radio based tag can receive an interrogation signal from the wireless sensor reader 130, and then wirelessly communicate the sensor data 106 back to the wireless sensor reader 130 as the tag data 132 and/or as the sensor information 134 to the task determination module 108. Generally, the task determination module 108 may be implemented in any one or more of the wearable article 102 described in this example environment and/or as a component of the computing device 114, which may be implemented as a mobile phone carried by the user, or as a computing device or server device located in a healthcare environment, such as in a hospital or clinic.

In this example, the task determination module 108 implements features of the described wearable article for determining tasks. In implementations, the task determination module 108 may include independent processing, memory, and logic components functioning as a computing and/or electronic device integrated with the wearable article 102. Alternatively or in addition, the task determination module 108 can be implemented as a software application, such as computer-executable software instructions that are executable with a processor or processing system 136 of the computing device 114. As a software application, the task determination module 108 can be stored on computer-readable storage memory 138 (e.g., device memory), or with any suitable memory device or electronic data storage implemented with the computing device 114.

The task determination module 108 can receive the sensor data 106 stored in memory 120 of the wearable article tag 116 and a state of the delivery device 110 from the memory 122 of the delivery device tag 118, and store the received data (also tag data 132) as the sensor information 134. The sensor information 134 may include information about the sensors 104 associated with the collected sensor data 106. The task determination module 108 can then use the sensor information 134 to determine a task performed by a user who is wearing the wearable article 102 while handling the delivery device 110. The task can be determined by comparing a pattern of movements and forces determined from sensor information 134 with known task patterns 140 of use of the delivery device. For instance, the sensor information 134 may indicate finger movements and applied pressure that matches a known task pattern of use for picking up the delivery device 110 and injecting a liquid (e.g., medicine) from the delivery device into a patient.

The task determination module 108 can also initiate to update the wearable article tag 116 and the delivery device tag 118 with a device state based on the determined task. Additional data from one or more other wireless radio based tags may also be considered and stored by the task determination module 108 in association with determining the task. For instance, the other wireless radio based tags may identify a location where the task was performed, a medication with which a delivery device was filled, a patient near whom the task was performed, and so on. The information from these other wireless radio based tags may be used to track equipment, to ensure that correct medications are administered to patients, and so on.

In implementations, the task determination module 108 can also determine whether a task was performed correctly by comparing the sensor data 106 (e.g., the sensor information 134 and/or the tag data 132) with a corpus of feedback data 142 related to the determined task. The corpus of feedback data 142 can be a periodically updated set of data from one or more users, or can reflect data only related to a particular user. The corpus of feedback data 142 includes an acceptable range for the values of the sensor data 106 for different tasks, and can include ranges for each of the sensors 104. The acceptable range for the performance of a task can be determined based on the corpus of feedback data 142 (e.g., acceptable within one standard deviation from the mean) or can be manually entered (e.g., acceptable if the pressure is within ten percent of a given value). The corpus of feedback data 142 can include a wide variety of data beyond the sensor data 106, such as patient outcomes related to particular tasks and the information from the other wireless radio based tags. Additionally, the sensor data can be associated with the wearable article tag 116, the delivery device tag 118, and/or a user who wears the wearable article 102 and handles the delivery device 110.

An indication of how a task was performed in comparison to the corpus of feedback data 142 and/or an acceptable range can be provided to the user who wears the wearable article 102 and handles the delivery device 110. The indication may be provided in the form of an audible and/or visual notification sent to the computing device 114, which may be the user's mobile device, or to a computing device, or may be provided as haptic feedback via the wearable article 102. In a training scenario, the indication may include one or more tips for improving performance of the task, or may include a comparison to previous performances of the task. The indication can also be visually displayed by the computing device or may be played through a speaker of the device as audible feedback. A notification may be initiated when a task is performed outside of the acceptable range of task performance, and may include next steps for correcting the incorrectly performed task. The corpus of feedback data 142 may, for instance, indicate that when a particular task is performed with sensor data values above an acceptable range, the patient often experiences extreme swelling. Accordingly, a notification is generated so that the user can take appropriate action to mitigate the swelling in the patient. Alternatively or in addition, the indication or notification can be provided in real-time while the task is being performed.

Example methods 200 and 300 are described with reference to respective FIGS. 2 and 3 in accordance with implementations of a wearable article for determining a task. Generally, any services, components, modules, methods, and/or operations described herein can be implemented using software, firmware, hardware (e.g., fixed logic circuitry), manual processing, or any combination thereof. Some operations of the example methods may be described in the general context of executable instructions stored on computer-readable storage memory that is local and/or remote to a computer processing system, and implementations can include software applications, programs, functions, and the like. Alternatively or in addition, any of the functionality described herein can be performed, at least in part, by one or more hardware logic components, such as, and without limitation, Field-programmable Gate Arrays (FPGAs), Application-specific Integrated Circuits (ASICs), Application-specific Standard Products (ASSPs), System-on-a-chip systems (SoCs), Complex Programmable Logic Devices (CPLDs), and the like.

Figure 2:
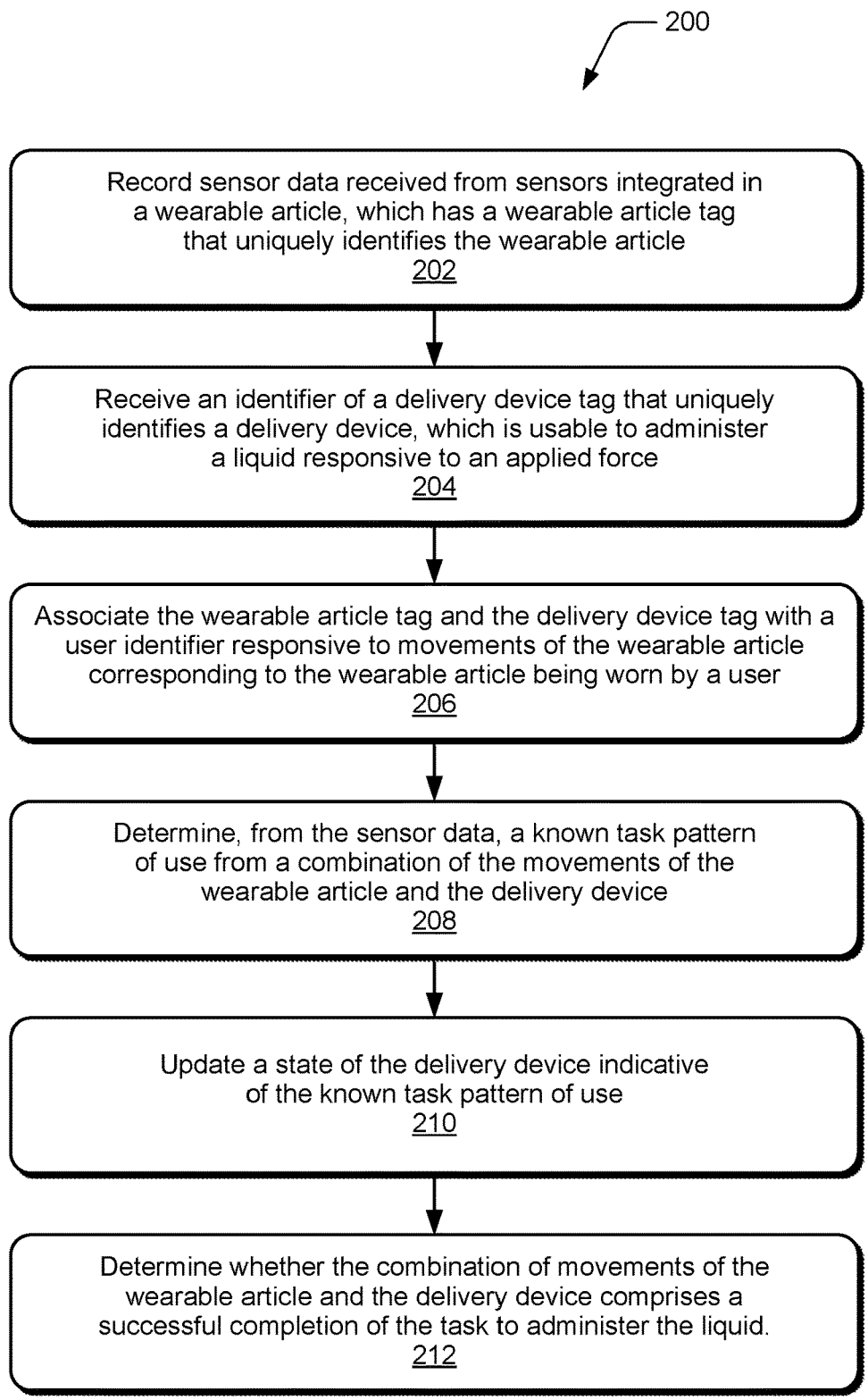
FIG. 2 is an example method of a wearable article for determining a task in accordance with one or more implementations of the techniques described herein.

FIG. 2 illustrates example method(s) 200 of a wearable article for determining a task as described herein, and is generally described with reference to the task determination module 108 that can be implemented in or communicatively connected to the wearable article 102. The order in which the method is described is not intended to be construed as a limitation, and any number or combination of the described method operations can be performed in any order to perform a method, or an alternate method.

At 202, sensor data is recorded as received from sensors integrated in the wearable article, which has a wearable article tag that uniquely identifies the wearable article. For example, the wearable article tag 116 receives the sensor data 106 from the sensors 104 of the wearable article 102, and records the sensor data 106 in the memory 120 of the wearable article tag. Alternatively or in addition, the wearable article tag 116 may facilitate communicating the sensor data 106 to the task determination module 108 to be recorded as the sensor information 134 and/or to the computing device 114 as the tag data 132. The sensor information 134 may be incorporated into the corpus of feedback data 142 and associated with one of the known task patterns 140 of use. The sensor data 106 can be received from each of the sensors 104, and indicates movements of the wearable article 102, the user wearing the wearable article 102 while handling the delivery device 110, and forces applied through the wearable article. In implementations, the delivery device 110 is a syringe usable to administer a liquid responsive to the applied force 112.

At 204, an identifier of a delivery device tag that uniquely identifies a delivery device is received, and the delivery device is usable to administer a liquid responsive to an applied force. For example, the task determination module 108 can receive the device identifier 124 of the delivery device tag 118 and associate the device identifier 124 with the article identifier 126 of the wearable article 102. Alternatively or in addition, the task determination module 108 can initiate to associate the device identifier 124 of the delivery device tag 118, the article identifier 126 of the wearable article tag 116, and the user identifier 128 stored in the memory 120 of the wearable article tag 116.

At 206, the wearable article tag and the delivery device tag are associated with a user identifier responsive to movements of the wearable article corresponding to the wearable article being worn by a user. For example, the task determination module 108 associates the device identifier 124 of the delivery device tag 118, the article identifier 126 of the wearable article tag 116, and the user identifier 128. The user identifier can be determined from various sources, such as from an employee badge having an RFID chip, identifying the user based on their mobile device, recognizing one or more biometric traits of the user, or having the user enter a username and password. By identifying the user, and associating the user with the wearable article 102 and the delivery device 110, the task determination module 108 is able to track actions taken by the particular user who wears the wearable article 102 and handles the delivery device 110. This can be used for training scenarios such as initially teaching a user a task, or identifying when a user needs to be retrained in a particular task. This provides oversight that is not practical or possible in a regular hospital or clinical setting.

At 208, a known task pattern of use for a combination of the movements of the wearable article and the delivery device is determined based on the sensor data. For example, the task determination module 108 determines, based on the sensor data (e.g., sensor information 134 and/or tag data 132), a known task pattern 140 of use for a combination of the movements of the wearable article 102 and the delivery device 110. The known task pattern 140 is one of the known task patterns 140 of use, and a pattern of sensor data 106 is compared to the known task patterns of use. For instance, the sensor data 106 may indicate finger movements of the wearable article 102 and a force amount and force direction of the applied force 112 that matches a known pattern for picking up the delivery device 110, the delivery device being filled with the liquid (e.g., medicine or other solution), and injecting the liquid from the delivery device into a patient.

At 210, a state of the delivery device is updated based on the known task pattern of use. For example, the task determination module 108 can initiate updating the delivery device tag 118, which then enables the delivery device tag to communicate its current use state to the wearable article 102 and/or to the task determination module 108. For instance, if a first user picked up and filled the delivery device 110 with a liquid solution, and then handed the filled delivery device to a second user to administer the injection, the second user's wearable article would be able to determine the state of the delivery device 110, and be able to communicate that back to the task determination module 108 to more quickly and accurately determine the task from the known task patterns.

At 212, a determination is made as to whether the combination of movements of the wearable article and the delivery device comprises a successful completion of the task to administer the liquid. For example, the task determination module 108 determines, based on the sensor data 106 and the corpus of feedback data 142 associated with the known task patterns 140 of use, whether the combination of movements of the wearable article 102 and the delivery device 110 comprises a successful completion of the task to administer the liquid.

Figure 3:
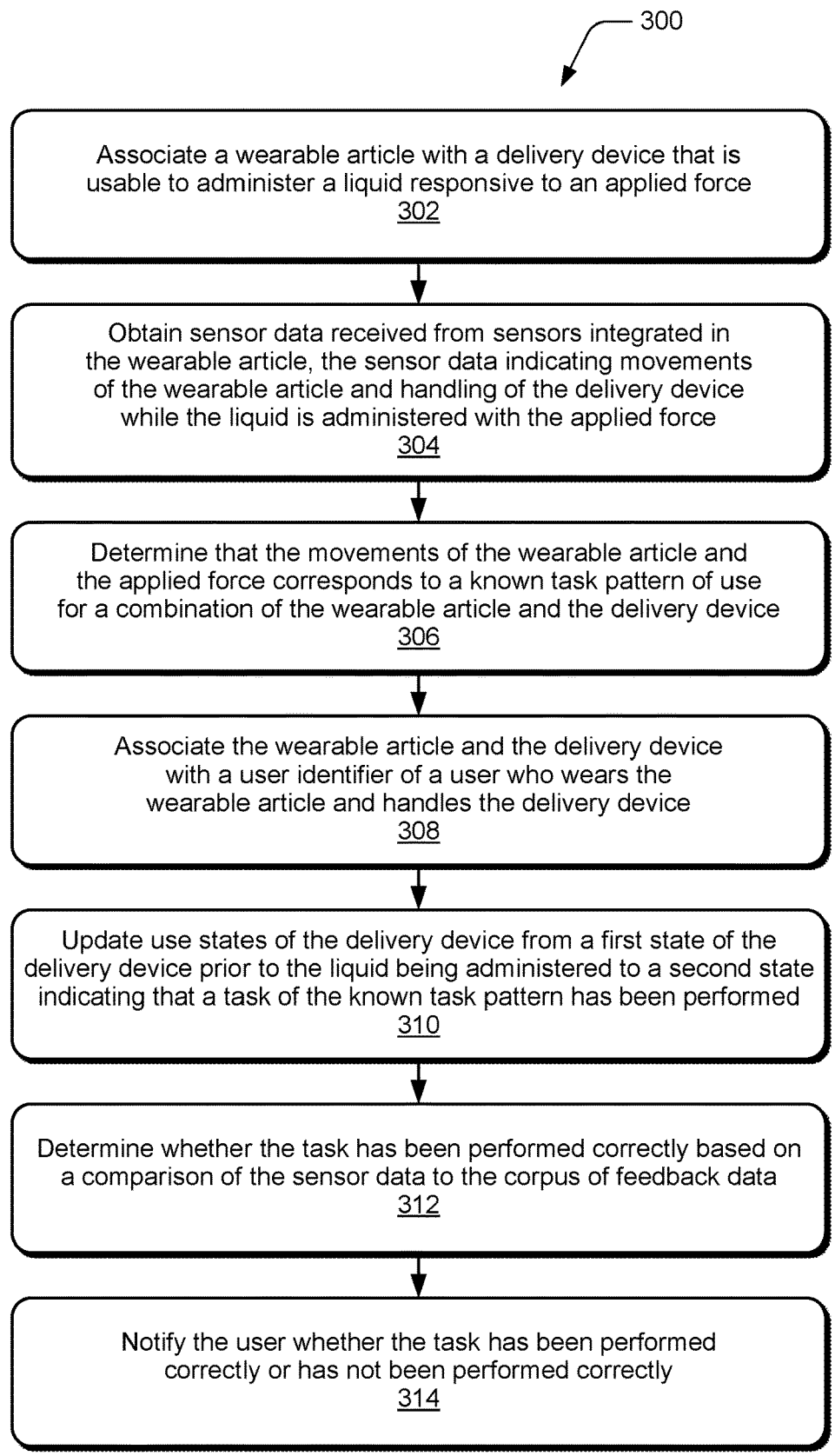
FIG. 3 is an example method of a wearable article for determining a task in accordance with one or more implementations of the techniques described herein.

FIG. 3 illustrates example method(s) 300 of a wearable article for determining a task as described herein, and is generally described with reference to the task determination module 108 that can be implemented in or communicatively connected to the wearable article 102. The order in which the method is described is not intended to be construed as a limitation, and any number or combination of the described method operations can be performed in any order to perform a method, or an alternate method.

At 302, a wearable article is associated with a delivery device that is usable to administer a liquid responsive to an applied force. For example, the task determination module 108 can initiate communication of the device identifier 124 of the delivery device tag 118, and the current state of the delivery device 110, to the wearable article tag 116. Associating the delivery device 110 with the wearable article 102 allows the task determination module 108 to associate actions taken by a user who is wearing the wearable article 102 with the correct delivery device. Further, identifying the delivery device 110 enables the task determination module 108 to track how and when the particular delivery device has been used. This information can be used for inventory tracking and/or incorporated in the corpus of feedback data 142 to determine, for instance, that a particular type of syringe is frequently misused.

At 304, sensor data received from sensors integrated in the wearable article is obtained, the sensor data indicating movements of the wearable article and handling of the delivery device while the liquid is administered with the applied force. For example, the wearable article tag 116 receives and records the sensor data 106 from the sensors 104 in the tag memory 120. Alternatively or in addition, the wearable article tag 116 may facilitate communicating the sensor data 106 to the task determination module 108 to be recorded as the sensor information 134. The sensor information 134 may be incorporated into the corpus of feedback data 142 and associated with one of the known task patterns 140 of use. The sensor data 106 can be received from each of the sensors 104, and indicates the movements of the wearable article 102, the user wearing the wearable article, and the applied force 112 through the wearable article 102. Additional data from other wireless radio based tags can be collected and stored as the sensor information 134, such as a location, a medication type, and/or a particular patient.

At 306, movements of the wearable article and the applied force is determined to correspond to a known task pattern of use for a combination of the wearable article and the delivery device based on the sensor data. For example, the task determination module 108 determines, from the sensor data 106 (e.g., as the sensor information 134 and/or the tag data 132), that the movements of the wearable article 102 in combination with the delivery device 110 corresponds to a known task pattern 140 of use of the delivery device. For instance, the sensor data 106, when compared to the corpus of feedback data 142, can indicate finger movements of the wearable article 102 and the applied force 112 that matches a known task pattern of use for picking up the delivery device 110, filling the delivery device with a liquid (e.g., medicine or other solution), and injecting the liquid from the delivery device 110 into a patient.

At 308, the wearable article and the delivery device are associated with a user identifier of a user who wears the wearable article and handles the delivery device. For example, the task determination module 108 associates the device identifier 124 of the delivery device tag 118, the article identifier 126 of the wearable article tag 116, and the user identifier 128 of the user who wears the wearable article 102 while handling the delivery device 110.

At 310, use states of the delivery device are updated from a first state of the delivery device prior to the liquid being administered to a second state indicating that a task associated with the known task pattern of use has been performed. For example, the task determination module 108 updates the use states of the delivery device 110, such as from a first state of the delivery device that indicates the delivery device contains the liquid, and to a second state that indicates the delivery device has been emptied of the liquid. Updating the delivery device tag 118 with the use states of the delivery device enables the delivery device tag 118 to communicate its state to the wearable article 102 and/or to the task determination module 108. For instance, if a first user picks up and fills the delivery device 110, and then hands the filled delivery device to a second user to administer an injection, then the second user's wearable article would know the state of the delivery device, and be able to communicate that to the task determination module 108 to more quickly and accurately determine the corresponding known task pattern 140 of use. The use states of the delivery device 110 may indicate any one or more of the known task patterns 140 of use. For instance, the first state may indicate that the delivery device is unused, and the second state may indicate that the delivery device is in use. Additional states include, but are not limited to, indicating that the delivery device has been filled and optionally indicating a liquid (e.g., medication or other solution) with which it is filled; indicating that the delivery device 110 has been emptied and optionally, that it was emptied correctly or incorrectly; that the delivery device 110 has been picked up and put down by a particular user; and so on.

At 312, a determination is made as to whether the task has been performed correctly based on a comparison of the sensor data to the corpus of feedback data associated with the task. For example, the The corpus of data 132 includes an indication of an acceptable range of values of sensor data 106 for different tasks. Comparing the sensor data 106 comprises determining if the sensor data 106 for each of the sensors 104 falls within the acceptable range for the determined task. For instance, the acceptable range can indicate an amount of pressure applied and a direction the pressure is applied.

At 314, the user is notified as to whether the task has been performed correctly or has not been performed correctly. For example, the task determination module 108 initiates an audible and/or visual notification to notify the user who is wearing the wearable article 102 and handling the delivery device 110 whether the task has been performed correctly, or has not been performed correctly. The results of task performance can be provided as visual, auditory, or haptic feedback, and can provide an indication of whether the sensor data 106 is within the acceptable range of performance, as compared to the corpus of feedback data 142. For instance, a graph can be displayed showing the range of all values in the corpus of feedback data 142 for a particular sensor for a particular task, and on that graph, the acceptable range of performance can be indicated as well as the value of the sensor data as performed. The range of all values may reflect the values of the user or of all users. The results may be accompanied by additional information, such as one or more tips for changing how the task is performed or remedial steps if the task was performed incorrectly.

Figure 4:
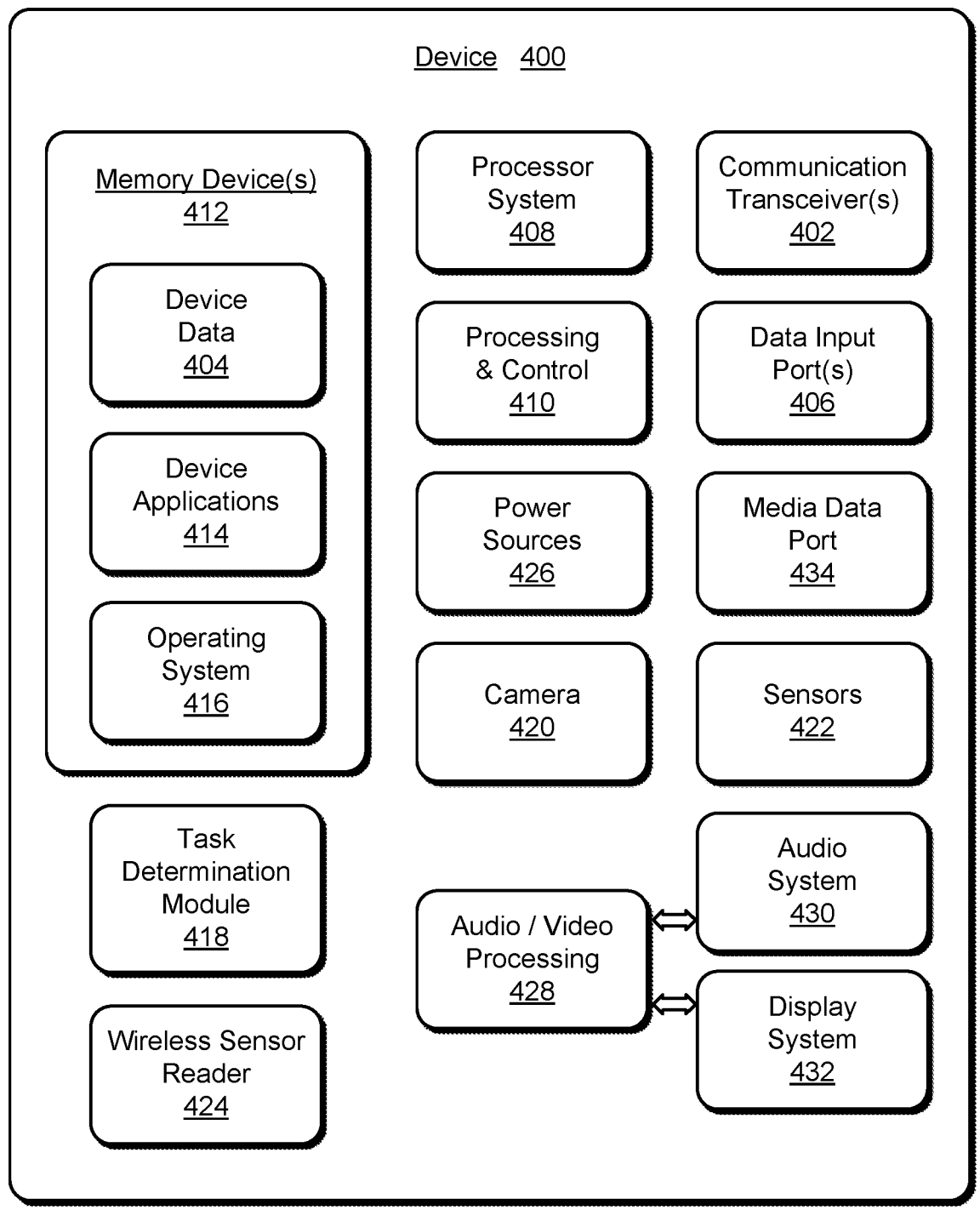
FIG. 4 illustrates various components of an example device that can implement aspects of a wearable article for determining a task.

FIG. 4 illustrates various components of an example device 400 in which aspects of a wearable article for determining a task can be implemented. The example device 400 can be implemented as any of the devices described with reference to the previous FIGS. 1-3, such as any type of mobile device, mobile phone, client device, wearable device, wearable article, server, tablet, computing, communication, entertainment, gaming, media playback, and/or other type of electronic device. For example, the wearable article 102, the task determination module 108, and the computing device 114 shown and described with reference to FIGS. 1-3 may be implemented as the example device 400. Further a wearable article or device may include any one or combination of a watch, armband, wristband, bracelet, glove or pair of gloves, glasses or goggles, jewelry items, clothing items, any type of footwear or headwear, wearable sensors, and/or other types of wearables, including a wearable item with integrated sensors.

The device 400 includes communication transceivers 402 that enable wired and/or wireless communication of device data 404 with other devices. The device data 404 can include any of the sensor data, sensor information, tag data, the known task patterns of use, and the corpus of feedback data. Additionally, the device data 404 can include any type of audio, video, and/or image data. Example communication transceivers 402 include wireless personal area network (WPAN) radios compliant with various IEEE 802.15 (Bluetooth™) standards, wireless local area network (WLAN) radios compliant with any of the various IEEE 802.11 (WiFi™) standards, wireless wide area network (WWAN) radios for cellular phone communication, wireless metropolitan area network (WMAN) radios compliant with various IEEE 802.16 (WiMAX™) standards, and wired local area network (LAN) Ethernet transceivers for network data communication.

The device 400 may also include one or more data input ports 406 via which any type of data, media content, and/or inputs can be received, such as user-selectable inputs to the device, messages, music, television content, recorded content, and any other type of audio, video, and/or image data received from any content and/or data source. The data input ports 406 may include USB ports, coaxial cable ports, and other serial or parallel connectors (including internal connectors) for flash memory, DVDs, CDs, and the like. The data input ports 406 may be used to couple the device to any type of components, peripherals, or accessories such as microphones, cameras, and/or sensors.

The device 400 includes a processor system 408 of one or more processors (e.g., any of microprocessors, controllers, and the like) and/or a processor and memory system implemented as a system-on-chip (SoC) that processes computer-executable instructions. The processor system 408 may be implemented at least partially in hardware, which can include components of an integrated circuit or on-chip system, an application-specific integrated circuit (ASIC), a field-programmable gate array (FPGA), a complex programmable logic device (CPLD), and other implementations in silicon and/or other hardware. Alternatively or in addition, the device can be implemented with any one or combination of software, hardware, firmware, or fixed logic circuitry that is implemented in connection with processing and control circuits, which are generally identified at 410. The device 400 may further include any type of a system bus or other data and command transfer system that couples the various components within the device. A system bus can include any one or combination of different bus structures and architectures, as well as control and data lines.

The device 400 also includes memory devices 412 which include computer-readable storage memory that enable data storage, such as data storage devices that can be accessed by a computing device, and that provide persistent storage of data and executable instructions (e.g., software applications, programs, functions, and the like). Examples of the memory devices 412 include volatile memory and non-volatile memory, fixed and removable media devices, and any suitable memory device or electronic data storage that maintains data for computing device access. The computer-readable storage memory can include various implementations of random access memory (RAM), read-only memory (ROM), flash memory, and other types of storage media in various memory device configurations. The device 400 may also include a mass storage media device.

The memory devices 412 provide data storage mechanisms to store the device data 404, other types of information and/or data, and various device applications 414 (e.g., software applications). For example, an operating system 416 can be maintained as software instructions with a memory device and executed by the processor system 408.

The device applications 414 may also include a device manager, such as any form of a control application, software application, signal-processing and control module, code that is native to a particular device, a hardware abstraction layer for a particular device, and so on.

In this example, the device 400 includes a task determination module 418 that implements aspects of a wearable article for determining a task, and may be implemented with hardware components and/or in software as one of the device applications 414, such as when the device 400 is implemented as the computing device 114 described with reference to FIGS. 1-3. Examples of the task determination module 418 include the task determination module 108 that is implemented as a software application and/or as hardware components. In implementations, the task determination module 418 may include independent processing, memory, and logic components as a computing and/or electronic device integrated with the device 400.

The example device 400 also includes a camera 420 and sensors 422. The sensors 422 can be implemented with various sensors, such as a gyroscope, an accelerometer, and/or other types of motion sensors to sense motion of the device and/or force sensors to detect applied forces. The various sensors 422 may also be implemented as components of an inertial measurement unit (IMU) in the device 400.

The device 400 also includes a wireless sensor reader 424, which may be implemented as a radio-frequency identification (RFID) reader that is implemented to interrogate RFID tags for identifying data and receive identification responses from the RFID tags. An example of the wireless sensor reader 424 is the wireless sensor reader 130 that is implemented as an integrated component of the computing device 114 and/or of the task determination module 108. In implementations, a wireless sensor reader as an attachment to the device 400 has an external power source. The device 400 can also include one or more power sources 426, such as when the device is implemented as a mobile device. The power sources 426 may include a charging and/or power system, and can be implemented as a flexible strip battery, a rechargeable battery, a charged super-capacitor, and/or any other type of active or passive power source.

The device 400 also includes an audio and/or video processing system 428 that generates audio data for an audio system 430 and/or generates display data for a display system 432. The audio system and/or the display system may include any devices that process, display, and/or otherwise render audio, video, display, and/or image data. Display data and audio signals can be communicated to an audio component and/or to a display component via an RF (radio frequency) link, S-video link, HDMI (high-definition multimedia interface), composite video link, component video link, DVI (digital video interface), analog audio connection, or other similar communication link, such as media data port 434. In implementations, the audio system and/or the display system are integrated components of the example device. Alternatively, the audio system and/or the display system are external, peripheral components to the example device.

Although implementations of a wearable article for determining a task have been described in language specific to features and/or methods, the subject of the appended claims is not necessarily limited to the specific features or methods described. Rather, the specific features and methods are disclosed as example implementations of a wearable article for determining a task, and other equivalent features and methods are intended to be within the scope of the appended claims. Further, various different examples are described and it is to be appreciated that each described example can be implemented independently or in connection with one or more other described examples. Additional aspects of the techniques, features, and/or methods discussed herein relate to one or more of the following:

A system comprising: a delivery device usable to administer a liquid responsive to an applied force, the delivery device including a delivery device tag that uniquely identifies the delivery device; a wearable article worn by a user while the liquid is administered via the delivery device with the applied force, the wearable article comprising: one or more sensors to detect movements of the wearable article and handling of the delivery device; a wearable article tag that uniquely identifies the wearable article, the wearable article tag including memory to store sensor data received from the one or more sensors, the sensor data identifying the movements of the wearable article and the applied force; a task determination module implemented to: receive the sensor data identifying the movements of the wearable article and the applied force from the wearable article tag; determine, from the sensor data, a task from a set of tasks associated with the delivery device that corresponds to the movements of the wearable article; determine whether the task was performed correctly based on a comparison of the sensor data to a correct pattern of use for the task.

Alternatively or in addition to the above described system, any one or combination of: the delivery device is a syringe, and the correct pattern of use for the task includes loading the syringe with the liquid and administering an injection. The delivery device tag and the wearable article tag comprise radio frequency identification (RFID) tags, the system further comprising a RFID reader implemented to: interrogate the delivery device tag and the wearable article tag; and receive the sensor data and an identification response from each of the delivery device tag and the wearable article tag. The task determination module is configured to: receive identification of the delivery device tag and the wearable article tag; associate the delivery device tag with the wearable article tag; and associate the task with the delivery device tag. The task determination module is configured to associate the wearable article tag with a user identifier responsive to the movements of the wearable article corresponding to the wearable article being worn by the user. The correct pattern of use is determined based on a corpus of data collected for the task, and the task is determined to be performed correctly if the sensor data falls within an accepted range indicated by the corpus of data. The one or more sensors comprise: one or more microelectromechanical systems (MEMS) to detect motion of the wearable article; and one or more force sensors to detect the applied force by the user wearing the wearable article.

A method comprising: recording sensor data received from one or more sensors integrated in a wearable article, the wearable article including a wearable article tag that uniquely identifies the wearable article; receiving an identifier of a delivery device tag that uniquely identifies a delivery device, the delivery device usable to administer a liquid responsive to an applied force; determining, from the sensor data, a known task pattern of use from a combination of movements of the wearable article and the delivery device; and updating, to the delivery device tag, a state indicative of the known task pattern of use.

Alternatively or in addition to the above described method, any one or combination of: determining that the known task pattern of use comprises administering the liquid from the delivery device. Associating the wearable article tag with a user identifier responsive to the movements of the wearable article corresponding to the wearable article being worn by a user. The known task pattern of use of the delivery device includes the delivery device being used to administer the liquid responsive to the applied force, as detected by the one or more sensors of the wearable article. The known task pattern of use of delivery device includes the delivery device being filled with the liquid, as detected by the one or more sensors of the wearable article. The delivery device is a syringe, and the known task pattern of use includes loading the syringe with the liquid and administering an injection. The known task pattern of use of the delivery device is further determined based on force data of the applied force as detected by the one or more sensors of the wearable article, the force data including a force amount and force direction. Further determining, based on the sensor data and a corpus of data associated with the known task pattern of use, whether the combination of movements of the wearable article and the delivery device comprises a successful completion of a task to administer the liquid. Further associating the delivery device tag with a user identifier of a user who wears the wearable article and handles the delivery device.

A method comprising: associating a wearable article with a delivery device that is usable to administer a liquid responsive to an applied force; obtaining sensor data received from one or more sensors integrated in the wearable article, the sensor data indicating movements of the wearable article and handling of the delivery device while the liquid is administered with the applied force; determining, from the sensor data, that the movements of the wearable article and the applied force corresponds to a known task pattern of use for a combination of the wearable article and the delivery device; and updating use states of the delivery device from a first state of the delivery device prior to the liquid being administered to a second state indicating that a task of the known task pattern has been performed.

Alternatively or in addition to the above described method, any one or combination of: the first state of the delivery device includes an indication that the delivery device contains the liquid, and the second state includes an indication that the delivery device has been emptied of the liquid. The determining comprises: receiving the sensor data from the one or more sensors of the wearable article; and comparing the sensor data to a corpus of data associated with the task to determine whether the task has been performed correctly. Further associating the wearable article and the delivery device with a user identifier of a user who wears the wearable article and handles the delivery device, and notifying the user if the comparison indicates that the task has not been performed correctly.

The invention claimed is:
1. A system, comprising:
a delivery device usable to administer a liquid responsive to an applied force, the delivery device including a delivery device tag that uniquely identifies the delivery device;
a wearable article worn by a user while the liquid is administered via the delivery device with the applied force, the wearable article comprising:
one or more sensors to detect movements of the wearable article and handling of the delivery device;
a wearable article tag that uniquely identifies the wearable article, the wearable article tag including memory to store sensor data received from the one or more sensors, the sensor data identifying the movements of the wearable article and the applied force;
a task determination module implemented to:
receive the sensor data identifying the movements of the wearable article and the applied force from the wearable article tag;
determine, from the sensor data, a task from a set of tasks associated with the delivery device that corresponds to the movements of the wearable article; and
determine whether the task was performed correctly based on a comparison of the sensor data to a correct pattern of use for the task.

2. The system of claim 1, wherein the delivery device is a syringe, and the correct pattern of use for the task includes loading the syringe with the liquid and administering an injection.

3. The system of claim 1, wherein the delivery device tag and the wearable article tag comprise radio frequency identification (RFID) tags, the system further comprising a RFID reader implemented to:
interrogate the delivery device tag and the wearable article tag; and
receive the sensor data and an identification response from each of the delivery device tag and the wearable article tag.

4. The system of claim 1, wherein the task determination module is configured to:
receive identification of the delivery device tag and the wearable article tag;
associate the delivery device tag with the wearable article tag; and
associate the task with the delivery device tag.

5. The system of claim 1, wherein the task determination module is configured to associate the wearable article tag with a user identifier responsive to the movements of the wearable article corresponding to the wearable article being worn by the user.

6. The system of claim 1, wherein the correct pattern of use is determined based on a corpus of data collected for the task, and the task is determined to be performed correctly if the sensor data falls within an accepted range indicated by the corpus of data.

7. The system of claim 1, wherein the one or more sensors comprise:
one or more microelectromechanical systems (MEMS) to detect motion of the wearable article; and
one or more force sensors to detect the applied force by the user wearing the wearable article.

8. A method, comprising:
recording sensor data received from one or more sensors integrated in a wearable article, the wearable article including a wearable article tag that uniquely identifies the wearable article;
receiving an identifier of a delivery device tag that uniquely identifies a delivery device, the delivery device usable to administer a liquid responsive to an applied force;
determining, from the sensor data, a known task pattern of use from a combination of movements of the wearable article and the delivery device; and
updating, to the delivery device tag, a state indicative of the known task pattern of use.

9. The method of claim 8, further comprising determining that the known task pattern of use comprises administering the liquid from the delivery device.

10. The method of claim 8, further comprising associating the wearable article tag with a user identifier responsive to the movements of the wearable article corresponding to the wearable article being worn by a user.

11. The method of claim 8, wherein the known task pattern of use of the delivery device includes the delivery device being used to administer the liquid responsive to the applied force, as detected by the one or more sensors of the wearable article.

12. The method of claim 8, wherein the known task pattern of use of delivery device includes the delivery device being filled with the liquid, as detected by the one or more sensors of the wearable article.

13. The method of claim 8, wherein the delivery device is a syringe, and the known task pattern of use includes loading the syringe with the liquid and administering an injection.

14. The method of 8, wherein the known task pattern of use of the delivery device is further determined based on force data of the applied force as detected by the one or more sensors of the wearable article, the force data including a force amount and force direction.

15. The method of claim 8, further comprising determining, based on the sensor data and a corpus of data associated with the known task pattern of use, whether the combination of movements of the wearable article and the delivery device comprises a successful completion of a task to administer the liquid.

16. The method of claim 8, further comprising associating the delivery device tag with a user identifier of a user who wears the wearable article and handles the delivery device.

17. A method, comprising:
associating a wearable article with a delivery device that is usable to administer a liquid responsive to an applied force;
obtaining sensor data received from one or more sensors integrated in the wearable article, the sensor data indicating movements of the wearable article and handling of the delivery device while the liquid is administered with the applied force;
determining, from the sensor data, that the movements of the wearable article and the applied force corresponds to a known task pattern of use for a combination of the wearable article and the delivery device; and
updating use states of the delivery device from a first state of the delivery device prior to the liquid being administered to a second state indicating that a task of the known task pattern has been performed.

18. The method of claim 17, wherein the first state of the delivery device includes an indication that the delivery device contains the liquid, and the second state includes an indication that the delivery device has been emptied of the liquid.

19. The method of claim 17, wherein the determining comprises:
receiving the sensor data from the one or more sensors of the wearable article; and
comparing the sensor data to a corpus of data associated with the task to determine whether the task has been performed correctly.

20. The method of claim 19, further comprising associating the wearable article and the delivery device with a user identifier of a user who wears the wearable article and handles the delivery device, and notifying the user if the comparison indicates that the task has not been performed correctly.

* * * * *